(12) United States Patent
Meglan et al.

(10) Patent No.: US 11,548,140 B2
(45) Date of Patent: Jan. 10, 2023

(54) SYSTEM AND METHOD FOR RADIO BASED LOCATION OF MODULAR ARM CARTS IN A SURGICAL ROBOTIC SYSTEM

(71) Applicant: Covidien LP, Mansfield, MA (US)

(72) Inventors: Dwight Meglan, Westwood, MA (US); Meir Rosenberg, Newton, MA (US); Robert W. Pierce, Franklin, MA (US); William J. Peine, Ashland, MA (US); Jaimeen Kapadia, Cambridge, MA (US); Eric J. Taylor, Southington, CT (US)

(73) Assignee: COVIDIEN LP, Mansfield, MA (US)

( * ) Notice: Subject to any disclaimer, the term of this patent is extended or adjusted under 35 U.S.C. 154(b) by 267 days.

(21) Appl. No.: 16/943,168

(22) Filed: Jul. 30, 2020

(65) Prior Publication Data
US 2021/0046637 A1    Feb. 18, 2021

Related U.S. Application Data

(60) Provisional application No. 62/887,004, filed on Aug. 15, 2019.

(51) Int. Cl.
*G05B 19/04* (2006.01)
*G05B 19/18* (2006.01)
(Continued)

(52) U.S. Cl.
CPC ............... *B25J 5/007* (2013.01); *A61B 34/30* (2016.02); *A61B 50/13* (2016.02); *B25J 9/1676* (2013.01);
(Continued)

(58) Field of Classification Search
CPC ........ B25J 5/007; B25J 9/1676; B25J 9/1697; A61B 34/30; A61B 50/13; A61B 90/50;
(Continued)

(56) References Cited

U.S. PATENT DOCUMENTS 10,338,596 B2 *   7/2019   Smid ................. B62D 15/0285
2009/0192524 A1*   7/2009   Itkowitz ................. A61B 34/30
                                                                606/130
(Continued)

FOREIGN PATENT DOCUMENTS

WO        2019204013  A1    10/2019

OTHER PUBLICATIONS

International Search Report dated Nov. 20, 2020 corresponding to counterpart Int'l Patent Application PCT/US2020/046281.
(Continued)

*Primary Examiner* — Harry Y Oh
(74) *Attorney, Agent, or Firm* — Carter, DeLuca & Farrell, LLP

(57) ABSTRACT

A position and tracking system for radio-based localization in an operating room, includes a receiver, a mobile cart, a processor, and a memory coupled to the processor. The mobile cart includes a robotic arm and a transmitter in operable communication with the receiver. The memory has instructions stored thereon which, when executed by the processor, cause the system to receive, from the transmitter, a signal including a position of the mobile carts in a 3D space based on the signal communicated by the transmitter and determine a spatial pose of the mobile carts based on the received signal.

20 Claims, 8 Drawing Sheets

(51) Int. Cl.
  *B25J 5/00* (2006.01)
  *G01S 11/06* (2006.01)
  *G05D 1/02* (2020.01)
  *B25J 9/16* (2006.01)
  *A61B 50/13* (2016.01)
  *A61B 34/30* (2016.01)
  *A61B 90/50* (2016.01)
  *A61B 34/20* (2016.01)

(52) U.S. Cl.
  CPC ............. *B25J 9/1697* (2013.01); *G01S 11/06* (2013.01); *G05D 1/028* (2013.01); *A61B 90/50* (2016.02); *A61B 2034/2051* (2016.02); *A61B 2034/2072* (2016.02)

(58) Field of Classification Search
  CPC .... A61B 2034/2051; A61B 2034/2072; A61B 90/361; A61B 2017/00017; A61B 2017/00123; A61B 2017/00128; A61B 2017/00207; A61B 2017/00221; A61B 2090/0811; A61B 2090/3975; A61B 34/20; G01S 11/06; G01S 5/14; G01S 5/163; G01S 19/14; G05D 1/028; G05D 1/0297; G05D 2201/0206; G08B 5/22; H04B 1/69; G16H 20/40; G16H 40/63; G05B 2219/40298
  See application file for complete search history.

(56) References Cited

U.S. PATENT DOCUMENTS

| | | | |
|---|---|---|---|
| 2009/0286548 A1* | 11/2009 | Coronel | H04W 4/20 455/456.1 |
| 2010/0256960 A1 | 10/2010 | Ortmaier et al. | |
| 2014/0163736 A1* | 6/2014 | Azizian | B25J 9/1676 700/259 |
| 2014/0276855 A1* | 9/2014 | de la Barrera | A61B 17/154 705/2 |
| 2014/0297130 A1* | 10/2014 | Griffiths | G05D 1/0011 701/41 |
| 2015/0100066 A1* | 4/2015 | Kostrzewski | A61B 90/06 606/130 |
| 2018/0344421 A1* | 12/2018 | Cagle | A61B 90/50 |
| 2019/0069962 A1* | 3/2019 | Tabandeh | A61B 34/32 |
| 2019/0231460 A1 | 8/2019 | DiMaio et al. | |
| 2019/0287063 A1* | 9/2019 | Skaaksrud | B65G 67/24 |
| 2022/0240878 A1* | 8/2022 | Reinhard | A61B 6/4441 |

OTHER PUBLICATIONS

Written Opinion completed Nov. 11, 2020 corresponding to counterpart Int'l Patent Application PCT/US2020/046281.
U.S. Appl. No. 62/660,476, filed Apr. 20, 2018, by Meglan et al.

\* cited by examiner

SYSTEM AND METHOD FOR RADIO BASED LOCATION OF MODULAR ARM CARTS IN A SURGICAL ROBOTIC SYSTEM

CROSS REFERENCE TO RELATED APPLICATIONS

This application claims the benefit of the filing date of provisional U.S. Patent Application No. 62/887,004, filed on Aug. 15, 2019.

FIELD

The present disclosure generally relates to a surgical robotic system having one or more modular arm carts each of which supports a robotic arm. More particularly, the present disclosure is directed to a system and method for radio-based location of the modular arm carts in a surgical robotic system in three-dimensional space.

BACKGROUND

Surgical robotic systems have become widely used by surgeons in surgical procedures because these systems enable surgery to be less invasive as compared to conventional open surgical procedures in which the surgeon is required to cut open large areas of body tissue. As a direct result thereof, robotic surgical systems minimize trauma to the patient and reduce patient recovery time and hospital costs. A hospital or surgical center may operate a surgical robotic system with multiple robotic arms. Knowing where the robotic arms are may be difficult. Accordingly, improvements are needed

SUMMARY

The techniques of this disclosure generally relate to a surgical robotic system having one or more modular arm carts, radio-based location of each of which in a 3D space is based on a signal communicated by the transmitter and determining a spatial pose of the mobile carts based on the received signal.

In accordance with aspects of the disclosure, a position and tracking system for radio-based localization in an operating room includes a receiver, a mobile cart, a processor, and a memory coupled to the processor. The mobile carts include a transmitter in operable communication with the receiver and a robotic arm. The memory having instructions stored thereon which, when executed by the processor, cause the system to receive, from the transmitter, a signal including a position of the mobile carts in a 3D space based on the signal communicated by the transmitter, and determine a spatial pose of the mobile carts based on the received signal.

In one aspect, the instructions, when executed, may further cause the system to determine a location to move the mobile carts based on at least one of a specific surgical procedure, a specific type of patient, a specific type of surgical table, or the configuration of an operating room and move the mobile carts to a new spatial pose based on the determined location and the received signal.

In another aspect, the disclosure provides that the transmitter may be a first transmitter. The system may further include a second transmitter located in proximity to a patient. The instructions, when executed, may further cause the system to determine a second spatial pose of the patient based on a signal communicated by the second transmitter and determine a position of the mobile cart relative to a patient based on the determined second spatial pose of the patient.

In accordance with aspects of the disclosure, the transmitter may include at least one of an RF transmitter, a microwave transmitter, or a millimeter-wave transmitter.

In an aspect of the present disclosure, the receiver may include a plurality of antennae.

In another aspect of the present disclosure, the signal for the transmitter may include a spread spectrum signal.

In yet another aspect of the present disclosure, the processor may be configured to determine the spatial pose of the mobile cart by receiving an indication by the receiver of a level of the signal from the transmitter.

In a further aspect of the present disclosure, the robotic arm may include a second transmitter in operable communication with the receiver.

In yet a further aspect of the present disclosure, the instructions, when executed, may further cause: the system to receive, from the second transmitter, a second signal including a position of the robotic arm in a 3D space based on the signal communicated by the second transmitter; and determine the spatial pose of the robotic arm based on the received second signal.

In yet another aspect of the present disclosure, the robotic arm may include a plurality of individual links. The plurality of links may include a plurality of transmitters in operable communication with the receiver.

In a further aspect of the present disclosure, the instructions, when executed, may further cause the system to receive, from the plurality of transmitters, a plurality of signals including a spatial pose of the plurality of individual links in a 3D space based on the plurality of signals communicated by the plurality of transmitters.

In yet a further aspect of the present disclosure, the instructions, when executed, may further cause the system to receive kinematic information from the robotic arm or camera positioning information from the robotic arm, receive shape information of the plurality of individual links, and cross-reference the spatial pose of the plurality of individual links with the kinematic information and/or camera positioning information.

In yet another aspect of the present disclosure, the system may further include a display. The instructions, when executed, may further cause the system to predict a possible collision with a second robotic arm based on the cross-reference and display an alert, on the display, indicating the possibility of a collision.

In accordance with aspects of the disclosure, a method of performing robotic surgery in an operating room includes receiving, from a transmitter of a movable cart supporting a robotic arm, a signal including a position of the mobile carts in a 3D space based on the signal communicated by the transmitter and determining a spatial pose of the mobile carts based on the received signal.

In a further aspect of the present disclosure, the method may further include determining a location to move the mobile carts within an operating room based on at least one of a specific surgical procedure, a specific type of patient, a specific type of surgical table, or a configuration of the operating room and moving the mobile carts to a new spatial pose based on the determined location and the received signal.

In yet a further aspect of the present disclosure, the transmitter may be a first transmitter. The method may further include receiving, from a second transmitter of a robotic arm of the movable cart, a second signal including a position of the robotic arm in a 3D space based on the signal communicated by the second transmitter and determining a spatial pose of the robotic arm based on the received second signal.

In yet another aspect of the present disclosure, the method may further include receiving, from a plurality of transmitters of individual links of the robotic arm, a plurality of signals including locations of each of the plurality of individual links in a 3D space based on the plurality of signals communicated by the plurality of transmitters and determining a spatial pose of each of the plurality of individual links of the robotic arm based on the received plurality of signals.

In a further aspect of the present disclosure, the method may further include determining a second spatial pose of a patient based on a signal communicated by the second transmitter located in proximity to a patient and determining a position of the mobile cart relative to a patient based on the determined second spatial pose of the patient.

In accordance with aspects of the disclosure, a non-transitory storage medium that stores a program causing a computer to execute a method for radio-based localization in an operating room, the method includes receiving, from a transmitter of a mobile cart, a signal including a position of the mobile carts in a 3D space based on the signal communicated by the transmitter and determining a spatial pose of the mobile carts based on the received signal.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Various aspects of the present disclosure are described herein with reference to the drawings wherein.

DETAILED DESCRIPTION

Figure 1:
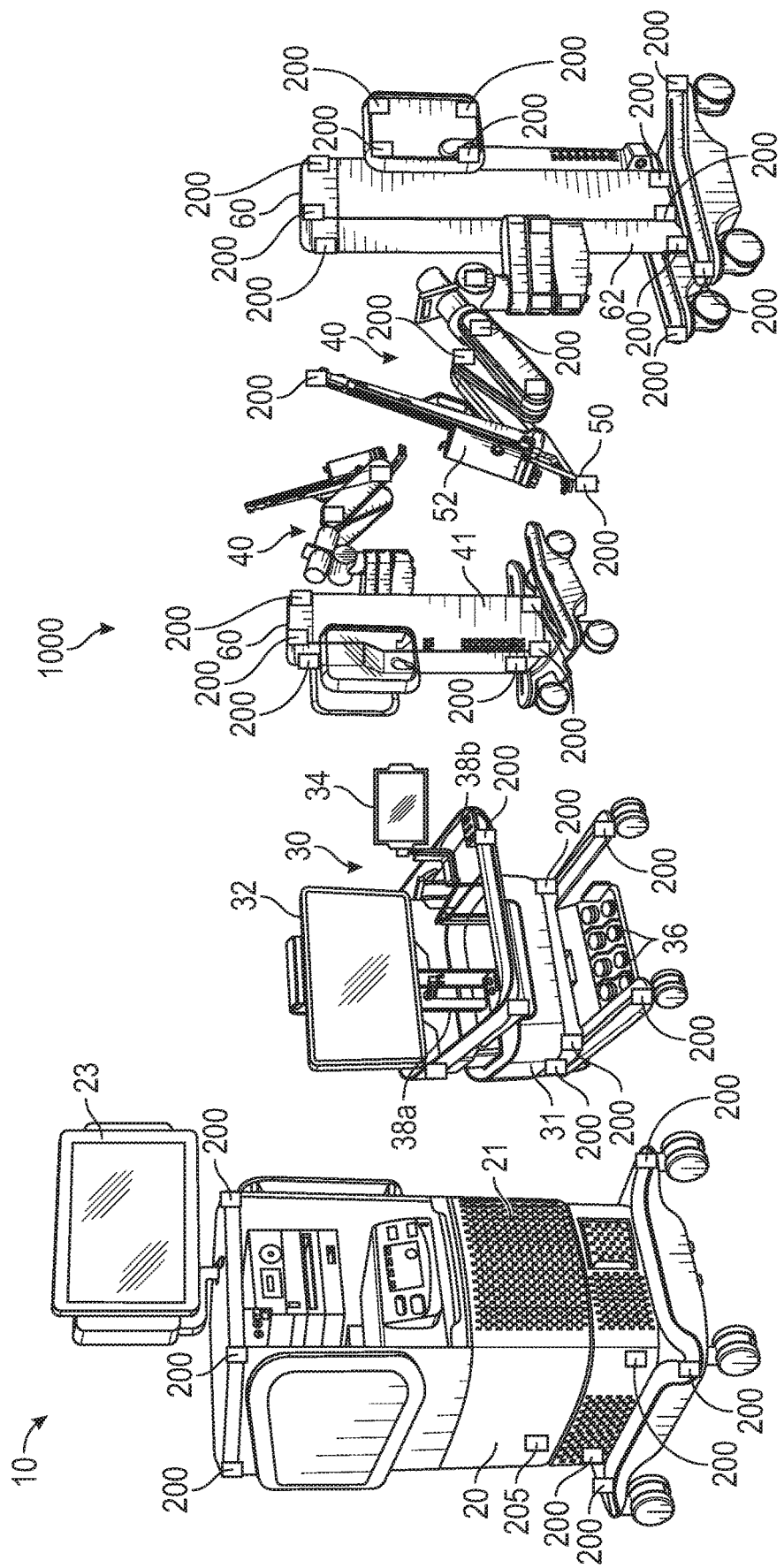
FIG. 1 is a schematic illustration of a surgical robotic system including a control tower, a console, and one or more surgical robotic arms according to the present disclosure.

Embodiments of the presently disclosed surgical robotic systems are described in detail with reference to the drawings, in which like reference numerals designate identical or corresponding elements in each of the several views. As used herein, the term "distal" refers to the portion of the surgical robotic system and/or the surgical instrument coupled thereto that is closer to the patient, while the term "proximal" refers to the portion that is farther from the patient.

Although the following description is specific to a surgical robotic system, the radio-based location system described below may be used with any suitable medical device requiring an alignment relative to a representative coordinate system or another orientation point. With reference to FIG. 1, a surgical robotic system 10 includes a control tower 20, which is connected to all of the components of the surgical robotic system 10, including a surgical console 30 and one or more robotic arms 40. Each of the robotic arms 40 includes a surgical instrument 50 removably coupled thereto. One or more of the robotic arms 40 may include an endoscope or a camera for observing the surgical site. The surgical instrument 50 is configured for use during minimally invasive surgical procedures. In embodiments, the surgical instrument 50 may be configured for open surgical procedures. Each of the robotic arms 40 is also coupled to a mobile cart 60.

The surgical console 30 includes a first display device 32, which displays a surgical site provided by cameras (not shown) disposed on the robotic arms 40, and a second display device 34, which displays a user interface for controlling the surgical robotic system 10. The surgical console 30 also includes a plurality of user interface devices, such as foot pedals 36 and a pair of handle controllers 38$a$ and 38$b$, which are used by a clinician to remotely control robotic arms 40.

The control tower 20 acts as an interface between the surgical console 30 and one or more robotic arms 40. In particular, the control tower 20 is configured to control the robotic arms 40, such as to move the robotic arms 40 and the corresponding surgical instruments 50, based on a set of programmable instructions and/or input commands from the surgical console 30, in such a way that robotic arms 40 and the surgical instrument 50 execute a desired movement sequence in response to input from the foot pedals 36 and the handle controllers 38$a$ and 38$b$. The control tower 20 includes a display 23 for displaying various information pertaining to the surgical robotic system 10.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein. Each of the control tower 20, the surgical console 30, and the robotic arm 40 includes a respective transmitter 200. It is contemplated that multiple transmitters 200 may be used.

Figure 2:
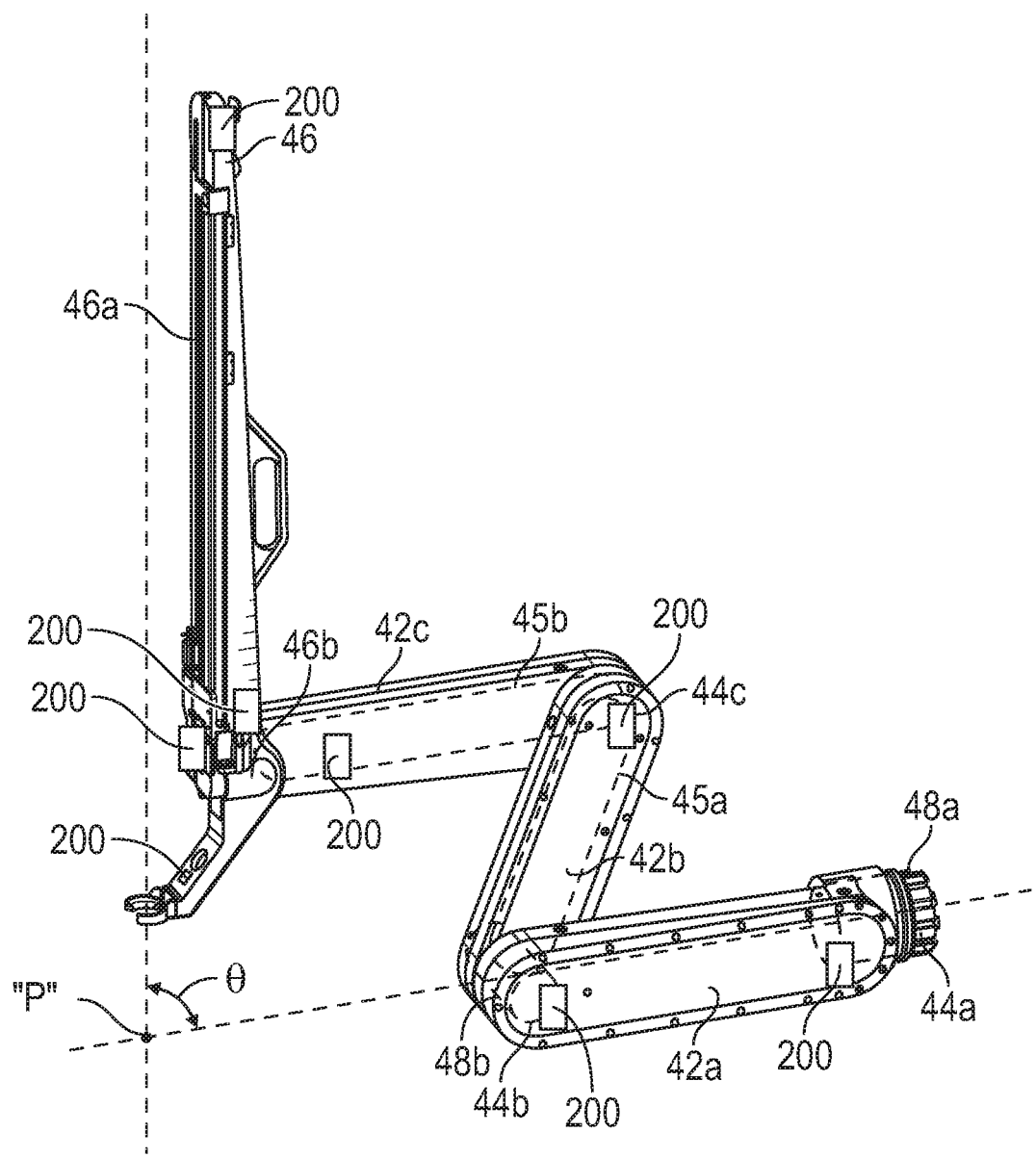
FIG. 2 is a perspective view of a surgical robotic arm of the surgical robotic system of FIG. 1 according to the present disclosure.
Figure 3:
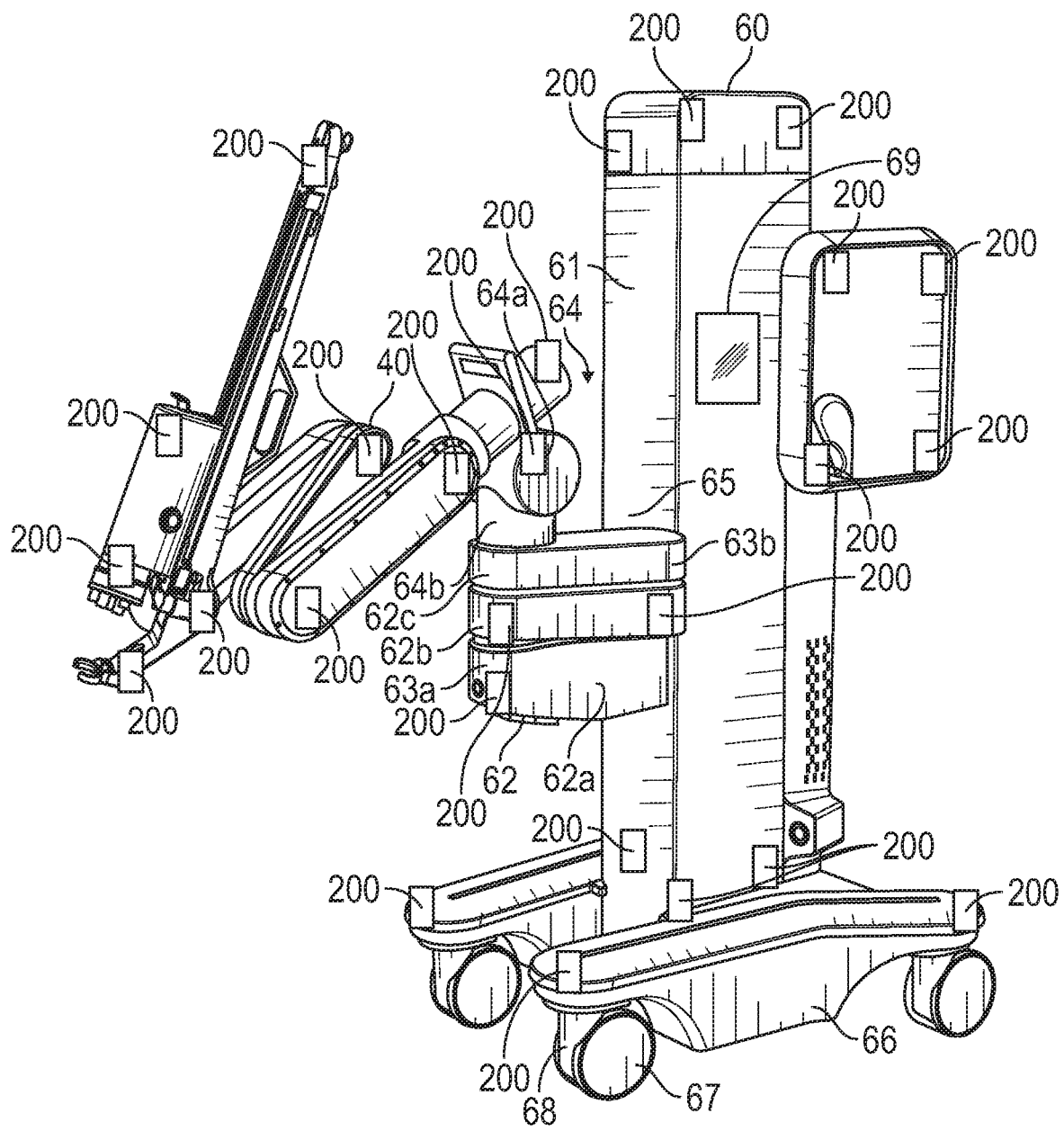
FIG. 3 is a perspective view of a setup arm with the surgical robotic arm of the surgical robotic system of FIG. 1 according to the present disclosure.

With reference to FIG. 2, each of the robotic arms 40 may include of a plurality of links 42a, 42b, 42c, which are interconnected at rotational joints 44a, 44b, 44c, respectively. The joint 44a is configured to secure the robotic arm 40 to the mobile cart 60 and defines a first longitudinal axis. With reference to FIG. 3, the mobile cart 60 includes a lift 61 and a setup arm 62, which provides a base for mounting of the robotic arm 40. The lift 61 allows for vertical movement of the setup arm 62. The mobile cart 60 includes a base 66 having a plurality of wheels 67, each of which having a brake 68. The mobile cart 60 also includes the cart display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at rotational joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis, which is perpendicular to a plane defined by the third link 62c, and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46a, which is configured to move the instrument drive unit 52 along the second longitudinal axis defined by the holder 46. The holder 46 also includes a rotational joint 46b, which rotates the holder 46 relative to the link 42c.

The joints 44a and 44b include an electrical actuator 48a and 48b configured to drive the joints 44a, 44b, 44c relative to each other through a series of belts 45a and 45b or other mechanical linkages such as a drive rod, a cable, or a lever and the like. In particular, the actuator 48b of the joint 44b is coupled to the joint 44c via the belt 45a, and the joint 44c is in turn, coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the pitch angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an electrical actuator to obviate the need for mechanical linkages.

Figure 4:
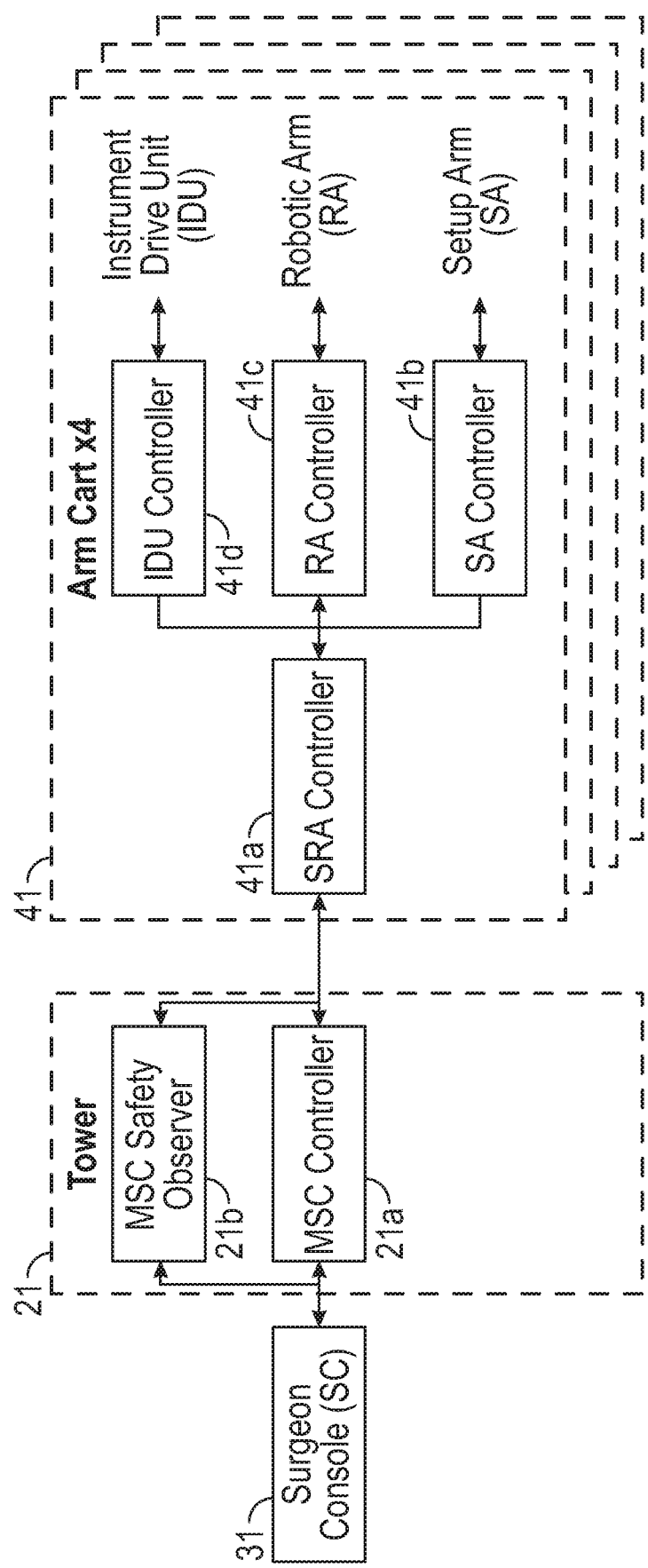
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the instrument drive unit 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the mobile cart 60, the robotic arm 40, and the instrument drive unit 52. The main cart controller 41a also communicates actual joint angles back to the controller 21a.

The setup arm controller 41b controls each of rotational joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed-loop position control. The robotic arm controller 41c calculates a movement command based on the calculated torque. The calculated motor commands are then communicated to one or more of the electrical actuators 48a and 48b in the robotic arm 40. The actual joint positions are then transmitted by the electrical actuators 48a and 48b back to the robotic arm controller 41c.

The IDU controller 41d receives desired joint angles for the surgical instrument 50, such as wrist and jaw angles, and computes desired currents for the motors in the instrument drive unit 52. The IDU controller 41d calculates actual angles based on the motor positions and transmits the actual angles back to the main controller 41a.

The robotic arm controller 41c is configured to estimate torque imparted on the rotational joints 44a and 44b by the rigid link structure of the robotic arm 40, namely, the links 42a, 42b, 42c. Each of the rotational joints 44a and 44b houses electrical actuator 48a and 48b. High torque may be used to move the robotic arm 40 due to the heavy weight of the robotic arm 40. However, the torque may need to be adjusted to prevent damage or injury. This is particularly useful for limiting torque during collisions of the robotic arm 40 with external objects, such as other robotic arms, patient, staff, operating room (OR) equipment, etc.

Figure 5:
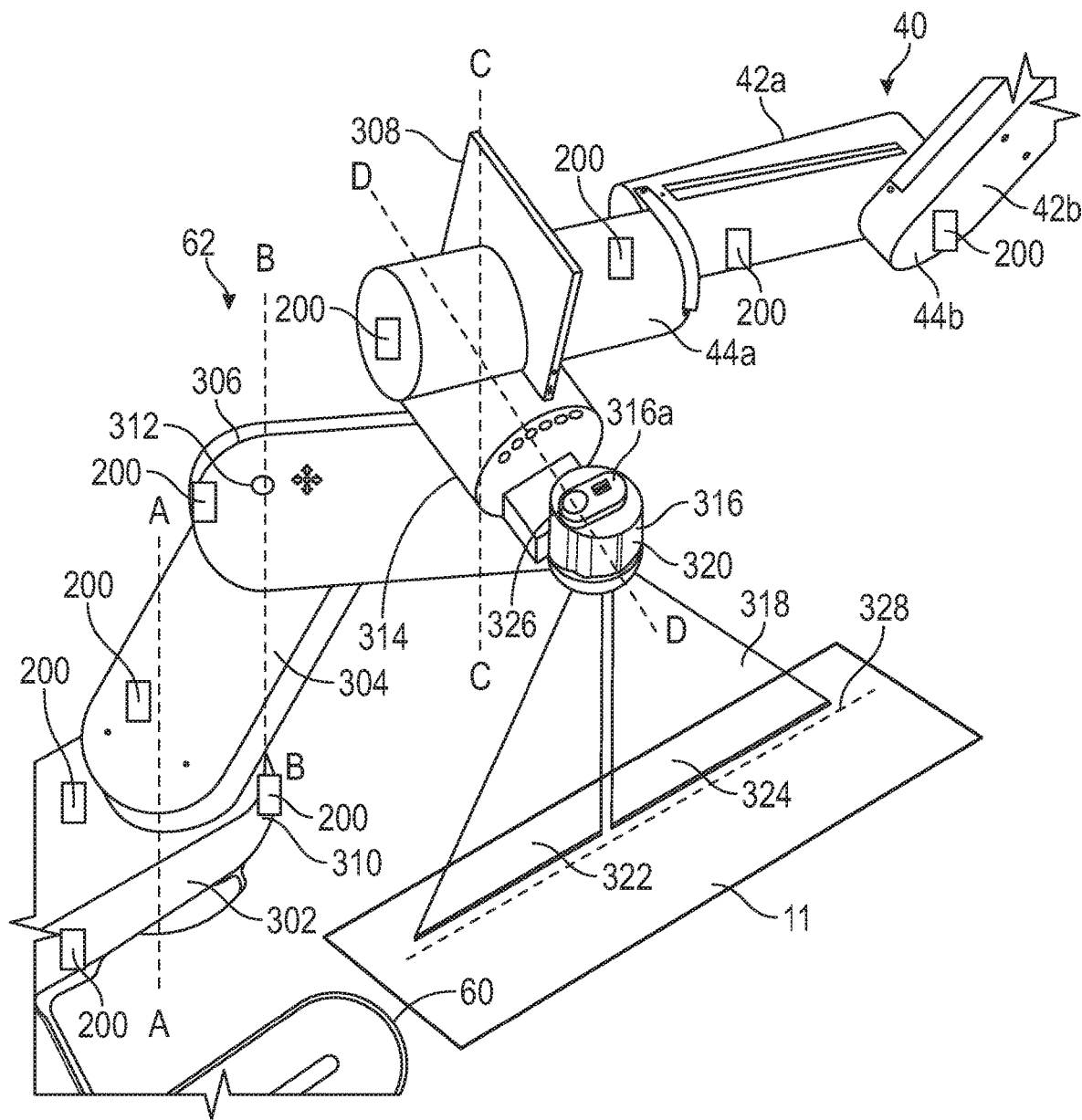
FIG. 5 is a perspective view of the setup arm and the robotic arm of the surgical robotic system of FIG. 1 according to the present disclosure.

With reference to FIG. 5, the robotic arm 40 may include one or more transmitters 200. The one or more transmitters 200 are in operable communication with the control tower 20. In embodiments, the transmitter 200 may be coupled directly to the coupling assembly 308. The transmitter 200 is configured to determine the orientation of the setup arm 62 and the robotic arm 40 relative to a representative coordinate system 11, which is a construct generated by the computer 21 and is used to virtually place and orient each of the robotic arms 40 to the clinician viewpoint, e.g., through a camera and/or an endoscope. In particular, the transmitter 200 may be used to create a common reference alignment for the robotic arm 40 and to determine the yaw orientation of the robotic arm 40 relative to the representative coordinate system 11. As used herein the term "yaw" denotes movement of the robotic arm 40 about a vertical axis perpendicular to the ground.

The orientation of each link of the robotic arm 40 and each setup link of the setup arm 62 is used in calculations to make the movement of the robotic arm 40 align with movements of input devices, e.g., manual inputs 18, at the surgical console 30. A light unit 412 (see FIG. 6) may be configured to project an alignment pattern 318 onto a horizontal surface. The alignment pattern 318 may be projected onto any surface, such as a surgical table, a floor, patient, or any other surface. The surface may not be completely horizontal as long as the alignment pattern 318 projected onto the surface is visible and discernable by a clinician or a computing device. Accordingly, any non-vertical surface may be used.

In embodiments, the robotic arm 40 may include an indicator 316a, such as a printed label or image on its surface to indicate a forward direction, or a direction relative to the patient. In further embodiments, the alignment pattern 318 may be a line having an indication of a direction. In embodiments, the alignment pattern 318 may include a first portion 324 and a second portion 322. The second portion 322 of the alignment pattern 318 may indicate a forward direction, or a portion of surgical instrument 50 and the robotic arm 40 closest to the patient, and the second portion 322 may indicate a backward direction, or a portion of surgical instrument 50 and the robotic arm 40 furthest from the patient. The second portion 322 and the first portion 324 may be visually different, such as different colors and/or patterns to allow for easier differentiation. In exemplary embodiments, the second portion 322 may be green, and the first portion 324 may be red. In embodiments, the second portion 322 may be blue, and the first portion 324 may be yellow to allow for better differentiating by colorblind personnel. In further embodiments, the second portion 322 and the first portion 324 may have different patterns, such as one of the first portion 324 or the second portion 322 may be solid whereas the other may be dashed.

Figure 6:
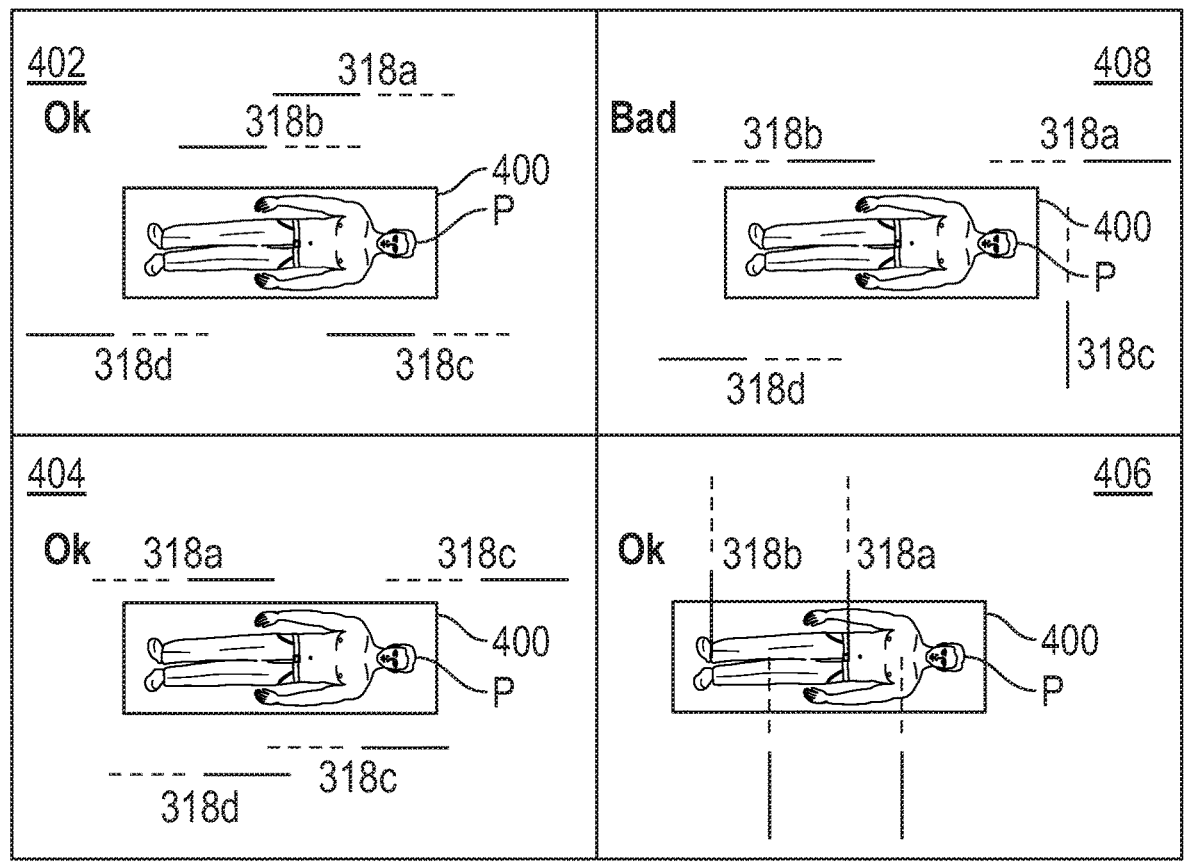
FIG. 6 is a schematic diagram of alignment patterns of the surgical robotic system of FIG. 1 according to the present disclosure.

With reference to FIG. 6, a surgical table 400 is shown with a patient "P" disposed thereon. FIG. 6 also shows a plurality of alignment patterns 318a, 318b, 318c, 318d being oriented relative to the surgical table 400. The surgical table 400 may be used as a reference point for orienting the robotic arms 40 by aligning each of their respective transmitters 200. The reference point may be any object that remains stationary during the period of alignment, such as the surgical table 400, the patient "P," a wall, a marking on the floor, or even any one of the other alignment patterns 318. The alignment patterns 318a, 318b, 318c, 318d projected by an alignment unit 316 of four robotic arms 40. The alignment pattern 318a is projected by the alignment unit 316 attached to the robotic arm 40 holding a camera and/or an endoscope. When properly oriented, the alignment patterns 318b, 318c, 318d are parallel to, and facing the same direction as the alignment pattern 318a projected from the robotic arm 40 holding the camera and/or the endoscope as shown in patterns 402, 404, and 406. Pattern 408 shows misaligned alignment patterns 318a, 318b, 318c, 318d, with the alignment pattern 318c being transverse relative to alignment patterns 318a and 318b and the alignment pattern 318d being oriented in an opposite direction than the alignment patterns 318a and 318b.

Figure 7:
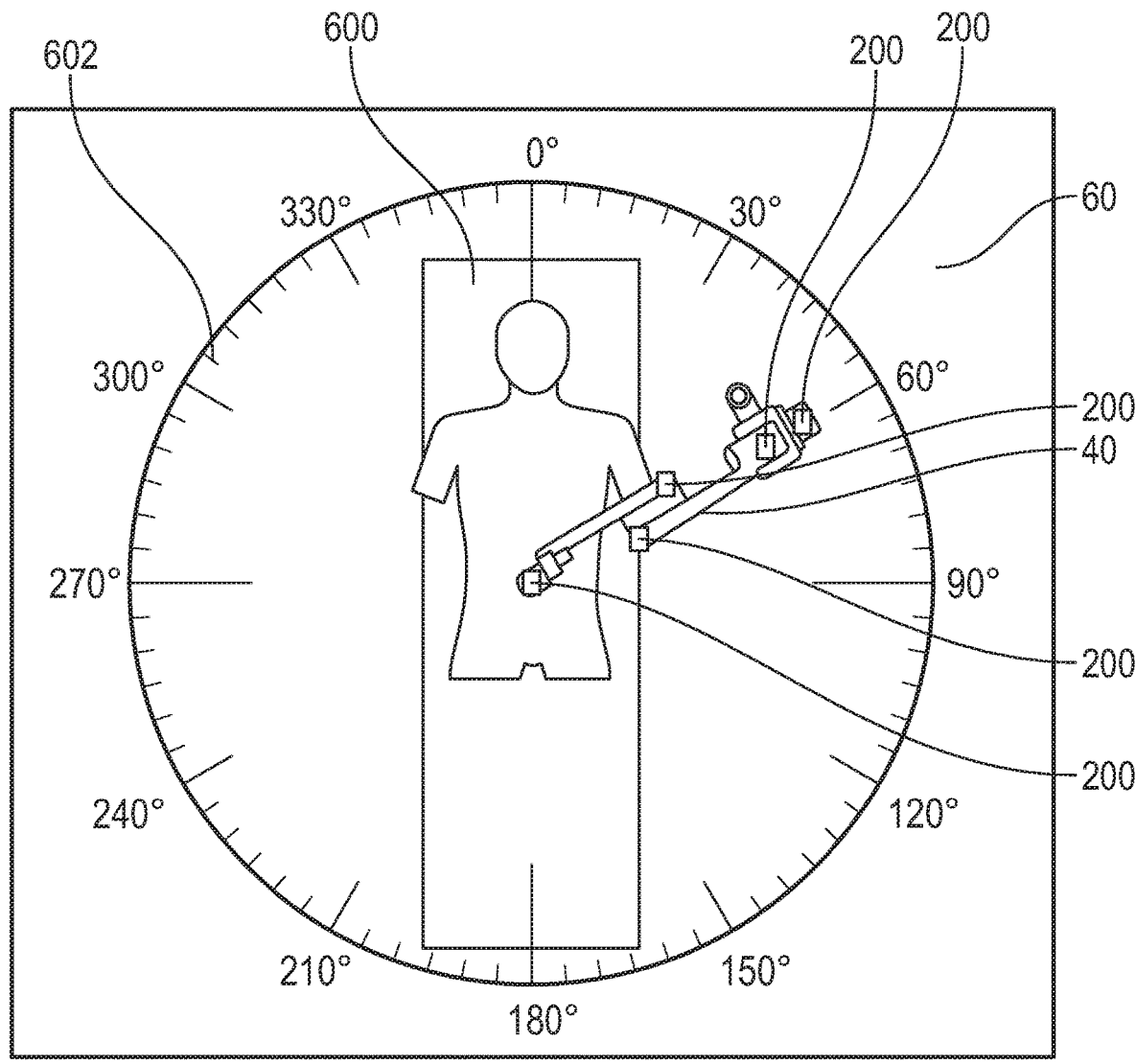
FIG. 7 is a schematic representation of a yaw angle of the robotic arm relative to a surgical table.

FIG. 7 shows a schematic diagram of the system 10 and in particular, the mobile cart 60 and the robotic arm 40, as represented by the controller 21a for storing the yaw angle $\phi$ for each of the robotic arm 40 (e.g., a longitudinal axis of the first link 42a of the robotic arm 40) relative to the surgical table 600. Although only one set of the mobile cart 60 and the robotic arm 40 is shown in FIG. 7, multiple mobile carts 60 and corresponding robotic arms 40 may be used. FIG. 7 shows a circular scale 602 having a degree scale from 0° to 360° being oriented with the top of the surgical table 600. In FIG. 7, the robotic arm 40 is shown as having the yaw angle $\phi$ of about 60°.

The circular scale 602 and the alignment angles shown thereon follow the right-hand rule (e.g., counter-clockwise), and are defined based on the angle from the alignment pattern 318 to the first link 42a of the robotic arm 40. The angle is zero when the second portion 322 of the alignment pattern 318 is aligned with a longitudinal axis defined by the first link 42a in a forward direction. Conversely, for the system setup and user interface 700, the alignment angle is defined clockwise. The angle is zero when the second portion 322 is aligned with the reverse direction of the first link 42a of the robotic arm 40.

The yaw angle is determined by transforming the raw angle of the alignment pattern 318 relative to the surgical table 600 into transformed alignment angle using the following formula (I): alignment angle=mod (3*π−raw alignment angle, 2*π)

In formula (I), the mod function is a modulo operation, which finds the remainder after division of the difference between 3*π and raw alignment angle by 2*π. The transformed alignment angle is then used to calculate the yaw angle using the formula (II):

yaw angle=transformed laser angle−sum(current vector−initial vector)

In formula (II), the initial vector is a 3×1 vector of the initial setup arm angles between the links 62a, 62b, 62c of the setup arm 62 prior to alignment, and the current vector is a 3×1 vector corresponding to the setup arm 62 being in the post-aligned state. As the robotic arm 40 is moved after its alignment, the current vector is updated, resulting in a new yaw angle being calculated. The yaw angle is displayed for each of the robotic arms 40 on a user interface. The user interface 700 may be displayed on the first display device 32 of the control tower 20 and/or the cart display 69 of the mobile cart 60.

When the mobile cart 60, along with the robotic arm 40 initially transitions into the aligned state, the yaw angle is equal to the alignment angle. As the setup arm 62 moves during manual plane motion to position the robotic arm 40 relative to the surgical table 600, the rotational joints 63a and 63b rotate about their individual rotation axis that are perpendicular to the floor, so each joint 63a and 63b additively contributes to the rotation of the base joint 44a of the robotic arm 40.

There are many situations in surgical robotics where knowing the spatial pose of one or more objects relative to another provides insight to enhance clinical performance. Recently, spread spectrum radio frequency sources and receivers have enabled millimeter resolution position sensing to be possible while not needing line of sight as well as not being sensitive to materials modifying the signals. Having this technology available allows the replacement of existing sensing approaches in surgery such as optical tracking of tools in spine and neurosurgery to allow performance to a predefined plan, but also enables entirely new uses of spatial location and pose sensing in the OR.

In accordance with the present disclosure, a position and tracking system 1000 for an absolute spatial position and pose tracking, for use in surgical robotics including spread spectrum radio frequency sources and receivers, is presented. The position and tracking system 1000 may include a transmitter 200, and a receiver 205, and be configured for use with or incorporated into a robotic surgical system 10, as shown in FIG. 1. The receiver 205 may include an RF receiver, a microwave receiver, and/or a millimeter-wave receiver. The receiver 205 may communicate with the computers 21, 31, 41 of FIG. 1. Briefly, the receiver 205 may include a processor (not shown) and memory (not shown). The receiver 205 may be located on control tower 20 of FIG. 1. It is contemplated that the receiver 205 may be integrated into the ceiling or integrated into the OR.

The transmitter 200 may include an RF transmitter, a microwave transmitter, and/or a millimeter-wave transmitter. In various aspects, a location of transmitter 200 (e.g., tracking units, beacons, or sensors) is desired to be tracked with millimeter precision relative to a transmitter 200. In various aspects, the position and tracking system 1000 may include one or more transmitters 200. In various aspects, the position and tracking system 1000 may include three or more of these transmitters 200, allowing the position and tracking system 1000 to determine and monitor the spatial pose of a rigid object to which they are mounted. For example, the position of the control tower 20 of FIG. 1 may be monitored in relation to a patient or the robotic arm 40, and vice-versa. In various aspects, the positions and poses of objects may be remotely monitored by the receiver 205 of the position and tracking system 1000, enabling the exemplary use cases described below. In various aspects, the position and tracking system 1000 determines an item's location in 3D based on data communicated by the transmitter 200.

In various aspects, the transmitters 200 may be mounted on and throughout the surgical robotic system 10, e.g., the spatial location of subcomponents of the surgical robotic system 10 can be monitored at all times including the mobile cart 60 of the robotic arms 40 as well as the individual links 42a, 42b, 42c of the arms even when they are within their sterile drapes. (See, e.g., FIG. 2 and FIG. 3.) With this capability, placement of the mobile cart 60, to optimal locations, can be ensured with the use of active guidance feedback, for a specific surgical procedure, for a specific type of patient, on the specific type of surgical table, in a specific configuration of an OR. In various aspects, by placing transmitters 200 at various locations on the robotic arm 40 and/or the mobile cart 60, and specifically along the individual links 42a, 42b, 42c of robotic arm 40, the individual links 42a, 42b, 42c of the robotic arm 40 may be constantly monitored, allowing the position and tracking system 1000 to know the locations, orientations and poses of all robotic arms 40 relative to one another at all times. In various aspects, this can be used as a double-check to ensure nothing has modified the state of the geometry of transmitters 200 on the robotic arm 40. Knowing where all the components of the robotic arm 40 are located relative to one another and adding the shape of those components to the known pose information, potential collisions of the robotic arms 40 can be detected and movements of the robotic arms 40 can be modified, the surgeon can be alerted that corrective action should be taken prior to a collision, or the robotic arm 40 movements can be halted to prevent such collision. In various aspects, the position and tracking system 1000 may use the known spatial pose information to determine the patient, operating table, and/or surgical personnel poses. In various aspects, the position and tracking system 1000 may provide collision avoidance based on at least one transmitter 200 on each the robotic arm 40 and at least one transmitter 200 on a surgical assistant or the patient.

In various aspects, transmitters 200 may be placed on or incorporated into surgical instrument ports (not shown). Specifically, in various aspects, the position and tracking system 1000 may include a transmitter 200 integrated into the access port or trocar (not shown) that is inserted into a patient's abdominal cavity. In various aspects, the position and tracking system 1000 may determine location information of the trocar or the access port to use as a setup guide. By the position and tracking system 1000 knowing the locations of surgical instrument ports, initial docking of the robotic system 10 to the surgical instrument ports can be performed under guidance, which will be especially beneficial as the OR team becomes familiar with the robotic surgical system 10. In addition, interactive guidance to, and confirmation of optimal placement for surgical ports for a specific patient and procedure will be possible. The position and tracking system 1000 is capable of continuously monitoring and assessing surgical instrument port movement, due to the deformation of patient tissue surrounding the surgical instrument port, and guidance provided by the robotic system 10 should excessive tissue movement be found.

In various aspects, the position and tracking system 1000 may track surgical tools (e.g., surgical instruments 50) used during surgery based on transmitters 200 located on/in the surgical tools. In various aspects, a transmitter 200 may be located at a surgical tool tip of a surgical instrument or on a known location of the surgical instrument, and by using the distance and relative positioning therebetween, a location of the surgical tool tip can be determined. For example, with the pose of a surgical instrument port and a pose of the last link 42c of the robotic arm 42 known and combined with the known kinematic state of the surgical tool, endpoint feedback of the surgical tool tips can be determined and continuously monitored such that the relative pose of all the surgical instruments relative to one another as well as relative to an endoscope, can be monitored. This provides an accurate and direct means of tool-tool and tool-camera pose monitoring.

In various aspects, the position and tracking system 1000 may use a plurality of transmitters 200 to determine input device (e.g., manual inputs 18) orientation/position. In various aspects, the position and tracking system 1000 microlocates the positioning of the input device with an integrated sensor.

In various aspects, surgical personnel may wear a single transmitter 200. In various aspects, the position and tracking system 1000 may determine and monitor personnel actions throughout a procedure to allow datasets to be built to provide predictive monitoring of surgery progress as well as detection of deviation from normative progress with appropriate notification of resources to ensure appropriate actions are taken. In various aspects, personnel may wear multiple transmitters 200. In various aspects, the position and tracking system 1000 may determine fine-grained detection of a possible collision with a robotic arm 40 and suggest remedial actions.

In various aspects, the wearing of multiple transmitters 200 also allows movements/gestures of personnel to be used as input to control communication amongst personnel using interactive methods such as augmented reality. In various aspects, transmitters 200 may be placed on the hands and/or feet of the surgeon, and the position and tracking system 1000 may monitor the movements of hands and/or feet of the surgeon, as a form of input to control/command the surgical robotic system 10, as an alternative to, or as an enhancement of linkage-based command input. In various aspects, the position and tracking system 1000 may include multiple transmitters 200 worn by multiple personnel involved in providing control inputs in complex operations. For example, the surgeon may wear a transmitter 200 on their foot to use as a virtual foot pedal. In various aspects, the position and tracking system 1000 may include one or more transmitters 200 on the surgeon to determine a location and/or orientation of the surgeon. In various aspects, the position and tracking system 1000 may use the location information to ensure that the surgeon is in the field of view of the user interface monitor and facing the screen. In various aspects, a transmitter 200 may be integrated on the glasses worn by the surgeon.

In various aspects, transmitters 200 may be placed on specific locations on a patient on the operating table. In this manner, patient location on the operating table can be known and confirmed, and this information can be combined with the surgical port tracking, robotic component tracking, and surgical personnel tracking. Benefits of such a complete and continuous spatial information portrait of the operating area include safety monitoring of the movements of the robotic arm 40 movements in relation to all aspects of personnel and equipment in the vicinity thereof. This information also allows adaption of movements of the robotic arms 40 to allow the operating table to be adjusted in the midst of a surgical procedure, thus saving time and enabling new types of surgical site access.

In various aspects, the position and tracking system 1000 may provide setup guidance for robotic system 10. For example, a transmitter 200 may be located on the patient, an operating table and/or one or more on each arm/cart. In various aspects, one or more transmitters 200 may be located on various sections of the operating table. For example, the position and tracking system 1000 can utilize the location information based on the data communicated from the transmitter 200 for operating table orientation.

In various aspects, the position and tracking system 1000 may locate robotic arms 40 and/or mobile carts 60 around the hospital. For example, the position and tracking system 1000 may determine that a robotic arm 40 or mobile cart 60 needed in the OR is currently located in a storage closet.

In various aspects, the position and tracking system 1000 may include transmitters 200 integrated into a wand that the surgeon can use to register parts or locations of a patient's anatomy. This can then be used for virtual walls and also aligning pre-operative scans to the user interface 700 and/or operating room team interface (ORTI) endoscope feeds. For example, the surgeon may touch the wand to an anatomical feature of a patient and press a button on the wand indicating the location of the feature.

In various aspects, the receiver may include a plurality of antennae. In various aspects, the receiver 205 transmits an RF signal (or a millimeter signal or a microwave signal) that is received by the receiver. In various aspects, the signal may be a spread spectrum signal. Spread spectrum is a form of wireless communications in which the frequency of the transmitted signal is deliberately varied. For example, a transmitter 200 may be located on a robotic arm 40 and may transmit a beacon at 30 GHz. It is contemplated that other frequencies may be used. The receiver 205, which may be located on the control tower 20, would receive the 30 GHz beacon signal from one or more transmitters 200 via the plurality of antennae of the receiver 205. The position and tracking system 1000 may utilize the level of the 30 GHz signal received at each of its antennae to determine the position data for the transmitter 200 in the OR. For example, the position and tracking system 1000 may determine the location data for the transmitter 200 based on triangulation. The position and tracking system 1000 may take this position data and cross-reference it with kinematic information and/or camera positioning information.

In accordance with this disclosure, the position and tracking system 1000 may be used to track the positions of the end effectors (or the tip) of the surgical instruments 50 for purposes of better accuracy. Currently, the instrument tip position is estimated based on the joint angles of the robotic arm 40. Additionally, bending of the shaft of the surgical instrument 50 or inaccurate joint angles add up and degrade accuracy. Accordingly, tracking the tip of the surgical instrument 50 provide a level of accuracy that is below millimeter dimensions and allows for image-guided procedures, surgical automation, and force estimates by estimating the bending of the surgical instrument 50.

It is additionally contemplated, and within the scope of this disclosure, that if the transmitters 200 are sufficiently small, and if the transmitters 200 are wireless (or tethered by only a thin wire), then the transmitters 200 may be placed directly within the patient's anatomy for tracking the position of organs and other anatomical structures. This could be used for image-guided surgery, updating deformable tissue models, and surgical automation since movement of the tissue, organ or anatomical structure of the patient is known.

Certain aspects of the radio frequency location operation are described in U.S. Provisional Patent Application Ser. No. 62/660,476, filed Apr. 20, 2018, by Meglan et al., the entire contents of which are hereby incorporated by reference herein.

While receiver 205 of the position and tracking system 1000 is described as being located on control tower 20, it is contemplated that receiver 205 of the position and tracking system 1000 may be located in the surgical console 30, in the operating table, or anywhere in/on the OR arena including the ceil or walls.

It will be understood that various modifications may be made to the embodiments disclosed herein. In embodiments, the transmitters 200 of the position and tracking system 1000 may be disposed on any suitable portion of the robotic arm. Therefore, the above description should not be construed as limiting, but merely as exemplifications of various aspects. Those skilled in the art will envision other modifications within the scope and spirit of the claims appended thereto.

In various aspects, the position and tracking system 1000 may be used as a capital management tool for hospitals to improve efficiency and/or increase utilization of equipment. For example, the position and tracking system 1000 may track the position and/or usage of all the system components across a hospital. The position and tracking system 1000 may record information regarding usage, downtime, location, and/or managers to help with utilization the modularity of a system. The recorded information may be input into a machine learning module as inputs to predict setup optimization. The position and tracking system 1000 may generate a report regarding the recorded information. For example, the position and tracking system 1000 may have a plurality of receivers located across the hospital, configured to locate a robotic arm anywhere in a hospital. This may reduce downtime between surgeries by allowing hospital staff to locate the nearest unused robotic arm. The position and tracking system 1000 may receive a request for an unused robotic arm 40 and provide a message to a user device, or a computing system indicating the location of the robotic arm in the hospital. In various aspects, the robotic arm may further include a GPS receiver and transmit the GPS data to the receiver. In aspects, the robotic arm 40 may include a beacon or a "find me" module. The robotic arm 40 may determine when a battery is below a threshold value and transmit the beacon and/or a message to a user based on the low battery. In various aspects, the position and tracking system 1000 may generate a spaghetti plot to visualize how equipment moves over a time period. The data may be analyzed by machine learning to provide a suggestion for more efficient use of the equipment (e.g., a robotic arm). In various aspects, the position and tracking system 1000 may compare surgical teams to determine best practices and share insights on more efficient use of the equipment. It is contemplated that the disclosed technology could be used to track devices other than medical devices, e.g., a copier for uses such as capital equipment tracking.

Operating room time is valuable. In aspects of the disclosure, the position and tracking system 1000 may be used to simplify the set-up process, cut down on OR turnover time, and reduce trip hazards. For example, the surgical table may include a transmitter 200. The type of procedure, habitus, and/or surgery for a patient may be used by the system 1000 to determine where ports need to go as well as where the robotic arm 40 should be located in the OR. For example, the data from the location and timing of the robotic arms 40 and mobile carts 60 may be recorded over time, over multiple procedures. This data may be used as training data for a machine learning network. In aspects, machine learning may be used for the determining. In an aspect, each of the robotic arms 40 may be assigned unique identification numbers based on their location around the patient. In an aspect, the system 1000 may automatically send the mobile carts 60 to an OR based on a scheduled procedure based on the predictions from the machine learning network. The machine learning network may include a neural network and/or a classifier. The machine learning network may predict, based on the training data and the type of procedure which OR will require which robotic arm 40. The mobile carts 60 and robotic arms 40 may automatically locate themselves around the surgical table in the proper OR based on the machine learning network.

Figure 8:
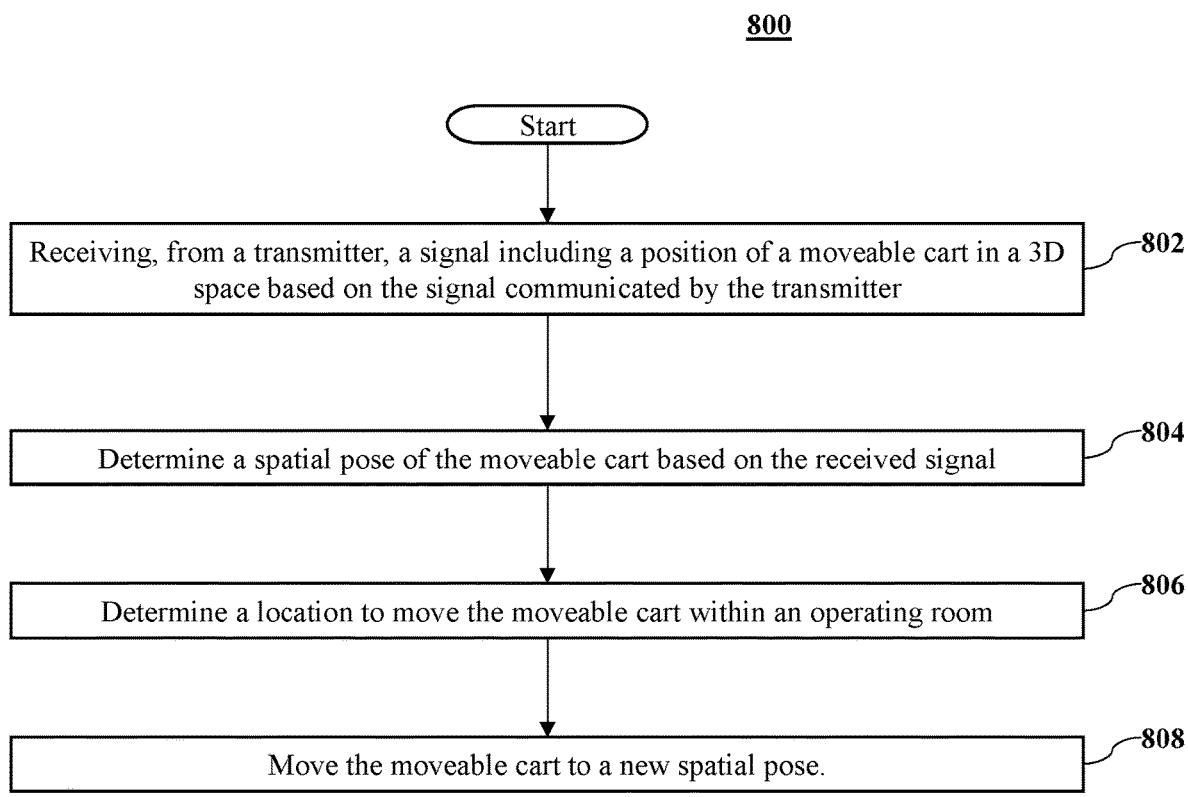
FIG. 8 is a flowchart of a method for radio-based location of components of a surgical robotic system in accordance with the disclosure.

The flow diagram of FIG. 8 described below include various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by the position and tracking system 1000, but those skilled in the art will appreciate that the position and tracking system 1000 is exemplary. In various aspects, the disclosed operations can be performed by another component, device, or system. In various aspects, the video system 230 or other component/device performs the actions or tasks via one or more software applications executing on the processor 252. In various aspects, at least some of the operations can be implemented by firmware, programmable logic devices, and/or hardware circuitry. Other implementations are contemplated to be within the scope of the disclosure.

Initially, at step 802, the system 1000 receives a signal from a transmitter 200 of a mobile cart 60 supporting a robotic arm 40. In aspects, the position of the mobile carts 60 in a 3D space is based on the signal communicated by the transmitter 200. For example, the transmitter 200 may include an RF transmitter, a microwave transmitter, and/or a millimeter-wave transmitter. The signal for the transmitter 200 may include a spread spectrum signal. In various aspects, the system 1000 may include one or more receivers configured to receive the signal from the transmitter 200. The receiver 205 may include a plurality of antennae.

Next, at step 804, the system 1000 determines a spatial pose of the mobile carts 60 based on the received signal. For example, the system 1000 may determine the spatial pose of the mobile cart(s) 60 by receiving an indication by the receiver 205 of a level of the signal from the transmitter 200.

Next, at step 806, the system 1000 determines a location to move the mobile carts 60 within an OR. In aspects, the determination may be based on a specific surgical procedure, a specific type of patient, a specific type of surgical table, and/or a configuration of the OR. For example, for a cardiovascular procedure or for a femoral-popliteal procedure, the patient may be in the supine position. For example, for cystoscopy, urology, and/or gynecology procedures, variations of lithotomy position are common. Surgical table accessories such as stirrups, split-leg positioners, and well leg-holders are commonly used to support patient legs during procedures. The surgical table may include additional attachments for these procedures. The surgical table and/or the attachments may include one or more transmitters 200 that the system 1000 uses to locate the surgical table and/or attachment when determining a location to move the mobile carts 60.

Next, at step 808, the system 1000 moves the mobile carts to a new spatial pose. In aspects, the new spatial pose may be based on the determined location and the received signal. For example, the system may determine that the mobile carts may In aspects, the robotic arm may include a transmitter 200 in operable communication with the receiver 205. The system 1000 may receive, from the transmitter 200 of the robotic arm 40, a signal including a position of the robotic arm in a 3D space based on the signal communicated by the transmitter 200 of the robotic arm 40 and determine the spatial pose of the robotic arm 40 based on the received signal.

In aspects, the robotic arm 40 may include a plurality of individual links, including a plurality of transmitters 200 in operable communication with the receiver 205. The system 1000 may receive, from the plurality of transmitters 200, a plurality of signals including a spatial pose of the plurality of individual links in a 3D space based on the plurality of signals communicated by the plurality of transmitters 200 of the individual links. The system 1000 may receive kinematic information from the robotic arm and/or camera positioning information from the robotic arm 40. The system 1000 may receive shape information of the plurality of individual links and cross-reference the spatial pose of the plurality of individual links with the kinematic information and/or camera positioning information. The system 1000 may predict a possible collision with a second robotic arm based on the cross-reference and display an alert, on a display, indicating the possibility of a collision. For example, the system 1000 may automatically set up the spatial pose of the robotic arm 40 based on a combination of the plurality of signals and a desired configuration that is optimal for the procedure.

In various aspects of the disclosure, the OR staff may wear transmitters 200 so that the system 1000 has a spatial awareness of the OR staff. This would help the system avoid collisions between the robotic arm 40 and the staff.

In aspects, the system 1000 may determine whether the mobile cart 60 is in the correct room. This may help with reducing OR turnaround time and/or locating capital equipment. For example, a particular mobile cart 60 may be in a first OR, when the system 1000 needs the mobile cart 60 in the second OR. The system 1000 may include a communication module to allow a node to node communication between the mobile carts 60 or the robotic arms 40. For example, the communication module may include 27 Mbps communication between the nodes. The system 100 would be able to register the nodes by triangulation of the communication modules.

In aspects, the system may include another transmitter 200 located in proximity to a patient (e.g., worn by the patient). In aspects, the system 1000 may determine a spatial pose of the patient based on a signal communicated by the transmitter 200 and determine a position of the mobile carts relative to a patient based on the determined spatial pose of the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A position and tracking system for radio-based localization in an operating room, the system comprising:
   a receiver;
   a mobile cart including:
      a transmitter in operable communication with the receiver; and
      a robotic arm;
   a processor; and
   a memory coupled to the processor, the memory having instructions stored thereon which, when executed by the processor, cause the system to:
      receive, from the transmitter, a signal including a position of the mobile cart in a 3D space based on the signal communicated by the transmitter;
      determine a spatial pose of the mobile cart based on the received signal; and
      determine a location to automatically move the mobile cart based on a specific surgical procedure, a specific type of patient, and a specific type of surgical table.

2. The system of claim 1, wherein the instructions, when executed, further cause the system to:
   further determine a location to move the mobile cart based on a configuration of an operating room; and
   automatically move the mobile cart to a new spatial pose based on the determined location and the received signal.

3. The system of claim 1, wherein the transmitter is a first transmitter, and wherein the system further includes a second transmitter located in proximity to a patient,
   wherein the instructions, when executed, further cause the system to:
      determine a second spatial pose of the patient based on a signal communicated by the second transmitter; and
      determine a position of the mobile cart relative to a patient based on the determined second spatial pose of the patient.

4. The system of claim 1, wherein the transmitter may include at least one of an RF transmitter, a microwave transmitter, or a millimeter-wave transmitter.

5. The system of claim 1, wherein the receiver includes a plurality of antennae.

6. The system of claim 1, wherein the signal for the transmitter includes a spread spectrum signal.

7. The system of claim 1, wherein the processor is configured to determine the spatial pose of the mobile cart by receiving an indication by the receiver of a level of the signal from the transmitter.

8. The system of claim 1, wherein the robotic arm includes a third transmitter in operable communication with the receiver.

9. The system of claim 8, wherein the instructions, when executed, further cause the system to:
receive, from the third transmitter, a second signal including a position of the robotic arm in a 3D space based on the signal communicated by the second transmitter; and
determine the spatial pose of the robotic arm based on the received second signal.

10. The system of claim 8, wherein the robotic arm includes:
a plurality of individual links, each of which include a plurality of fourth transmitters in operable communication with the receiver.

11. The system of claim 10, wherein the instructions, when executed, further cause the system to:
receive, from the plurality of transmitters, a plurality of signals including a spatial pose of the plurality of individual links in a 3D space based on the plurality of signals communicated by the plurality of transmitters.

12. The system of claim 11, wherein the instructions, when executed, further cause the system to:
receive at least one of kinematic information from the robotic arm or camera positioning information from the robotic arm;
receive shape information of the plurality of individual links; and
cross-reference the spatial pose of the plurality of individual links with the at least one of kinematic information or camera positioning information.

13. The system of claim 12, further comprising a display, wherein the instructions, when executed, further cause the system to:
predict a possible collision with a second robotic arm based on the cross-reference; and
display an alert, on the display, indicating the possibility of a collision.

14. A method of performing robotic surgery in an operating room, the method comprising:
receiving, from a transmitter of a mobile cart supporting a robotic arm, a signal including a position of the mobile cart in a 3D space based on the signal communicated by the transmitter;
determining a spatial pose of the mobile cart based on the received signal; and
determining a location to automatically move the mobile cart based on a specific surgical procedure, a specific type of patient, and a specific type of surgical table.

15. The method of claim 14, further comprising:
determining a location to move the mobile cart within an operating room based on at least one of a specific surgical procedure, a specific type of patient, a specific type of surgical table, or a configuration of the operating room; and
automatically moving the mobile cart to a new spatial pose based on the determined location and the received signal.

16. The method of claim 14, wherein the transmitter is a first transmitter, and further comprising:
receiving, from a second transmitter of a robotic arm of the mobile cart, a second signal including a position of the robotic arm in a 3D space based on the signal communicated by the second transmitter; and
determining a spatial pose of the robotic arm based on the received second signal.

17. The method of claim 16, further comprising:
receiving, from a plurality of transmitters of individual links of the robotic arm, a plurality of signals including locations of each of the plurality of individual links in a 3D space based on the plurality of signals communicated by the plurality of transmitters; and
determining a spatial pose of each of the plurality of individual links of the robotic arm based on the received plurality of signals.

18. The method of claim 16, further comprising:
determining a second spatial pose of a patient based on a signal communicated by the second transmitter located in proximity to a patient; and
determining a position of the mobile cart relative to a patient based on the determined second spatial pose of the patient.

19. The method of claim 14, further comprising determining the spatial pose of the mobile cart by receiving an indication by the receiver of a level of the signal from the transmitter.

20. A non-transitory storage medium that stores a program causing a computer to execute a method for radio-based localization in an operating room, the method comprising:
receiving, from a transmitter of a mobile cart, a signal including a position of the mobile cart in a 3D space based on the signal communicated by the transmitter;
determining a spatial pose of the mobile cart based on the received signal; and
determining a location to automatically move the mobile cart based on at least one of a specific surgical procedure, a specific type of patient, and a specific type of surgical table.

\* \* \* \* \*